United States Patent [19]
Zelle et al.

[11] Patent Number: 5,840,736
[45] Date of Patent: Nov. 24, 1998

[54] METHODS AND COMPOSITIONS FOR STIMULATING NEURITE GROWTH

[75] Inventors: Robert E. Zelle, Stow; Michael Su, Newton, both of Mass.

[73] Assignee: Vertex Pharmaceuticals Incorporated, Cambridge, Mass.

[21] Appl. No.: 748,447

[22] Filed: Nov. 13, 1996

[51] Int. Cl.[6] .......................... A61K 31/44; A61K 38/18
[52] U.S. Cl. ........................ 514/332; 514/12; 514/341
[58] Field of Search .......................... 514/12, 332, 341

[56] References Cited

U.S. PATENT DOCUMENTS

| | | | |
|---|---|---|---|
| 5,543,423 | 8/1996 | Zelle et al. | 514/332 |
| 5,614,547 | 3/1997 | Hamilton et al. | 514/423 |
| 5,696,135 | 12/1997 | Steiner et al. | 514/317 |

FOREIGN PATENT DOCUMENTS

| | | |
|---|---|---|
| WO 96/15101 | 5/1996 | WIPO . |
| WO 96/40140 | 12/1996 | WIPO . |
| WO 96/40633 | 12/1996 | WIPO . |
| WO 97/16190 | 5/1997 | WIPO . |

OTHER PUBLICATIONS

J.P. Steiner et al., "High brain densities of the immunophilin FKBP colocalized with calcineurin," *Nature*, 358, pp. 584–587 (1992).

J.R. Hauske et al., "Design and synthesis of novel FKBP inhibitors," *J. Med. Chem.*, 35, pp. 4284–4296 (1992).

B.G. Gold et al., "FK506, an immunosuppressant, increases functional recovery and axonal regeneration in the rat following axotomy of the sciatic nerve," *Soc. Neurosci. Abs.*, 19, p. 1316 (1993).

B.G. Gold et al., "The immunosuppressant FK506 increases the Rate of Axonal Regeneration in Rat Sciatic Nerve," *J. Neuroscience.*, 15(11), pp. 7509–7516 (Nov., 1995).

W.E. Lyons et al., "Immunosupressant FK506 promotes neurite outgrowth in cultures of PC12 cells and sensory ganglia," *Proc. Natl. Acad. Sci. USA*, 91, pp. 3191–3195 (Apr., 1994).

John Sharkey et al., "Immunophilins mediate the neuroprotective effects of FK506 in focal cerebral ischaemia." *Nature*, 371, pp. 336–339 (Sep. 22, 1994).

W.E. Lyons et al., "Neuronal regeneration enhances the expression of the immunophilin FKBP-12," *J. Neuroscience.*, 15, pp. 2985–2994 (Apr., 1995).

*Primary Examiner*—William R. A. Jarvis
*Attorney, Agent, or Firm*—Fish & Neave; James F. Haley, Jr.; N. Govindaswamy

[57] ABSTRACT

The present invention relates to methods and pharmaceutical compositions for stimulating the growth of neurites in nerve cells. The compositions comprise a neurotrophic amount of a compound and a neurotrophic factor, such as nerve growth factor (NGF). The methods comprise treating nerve cells with the above compositions or compositions comprising the compound without a neurotrophic factor. The methods of this invention can be used to promote repair of neuronal damage caused by disease or physical trauma.

26 Claims, No Drawings

METHODS AND COMPOSITIONS FOR STIMULATING NEURITE GROWTH

TECHNICAL FIELD OF THE INVENTION

The present invention relates to methods and pharmaceutical compositions for stimulating the growth of neurites in nerve cells. The compositions comprise a neurotrophic amount of a compound and a neurotrophic factor, such as nerve growth factor (NGF). The methods comprise treating nerve cells with the above compositions or compositions comprising the compound without a neurotrophic factor. The methods of this invention can be used to promote repair of neuronal damage caused by disease or physical trauma.

BACKGROUND OF THE INVENTION

Neurological diseases are associated with the death or injury of neuronal cells. The loss of dopaminergic neurons in the substantia nigra is the etiological cause for Parkinson's disease. Although the molecular mechanism of neurodegeneration in Alzheimer's disease is yet to be established, it is clear that brain inflammation, and deposition of beta-amyloid protein and other such agents may inhibit the survival of neurons and mitigate the growth of neurites used for communication between neurons. In patients suffering from brain ischemia or spinal cord injuries, extensive neuronal cell death is observed. Currently, there are no satisfactory treatments for these diseases.

Typical treatment of neurological diseases involves drugs capable of inhibiting neuronal cell death. A more recent approach involves the promotion of nerve regeneration by promoting neurite outgrowth.

Neurite outgrowth, which is critical for the survival of neurons, is stimulated in vitro by nerve growth factors (NGF). For example, Glial Cell Line-Derived Neurotrophic Factor (GDNF) demonstrates neurotrophic activity both, in vivo and in vitro, and is currently being investigated for the treatment of Parkinson's disease. Insulin and Insulin-like growth factors have been shown to stimulate growth of neurites in rat pheochromocytoma PC12 cells and in cultured sympathetic and sensory neurons [Recio-Pinto et al., *J. Neurosci.*, 6, pp. 1211–1219 (1986)]. Insulin and Insulin-like growth factors also stimulate the regeneration of injured motor nerves in vivo and in vitro [Near et al., *PNAS*, pp. 89, 11716–11720 (1992); and Edbladh et al., *Brain Res.*, 641, pp. 76–82 (1994)]. Similarly, fibroblast growth factor (FGF) stimulates neural proliferation [D. Gospodarowicz et al., *Cell Differ.*, 19, p. 1 (1986)] and growth [M. A. Walter et al., *Lymphokine Cytokine Res.*, 12, p. 135 (1993)].

There are, however, several disadvantages associated with the use of nerve growth factors for treating neurological diseases. They do not readily cross the blood-brain barrier. They are unstable in plasma. And they have poor drug delivery properties.

Recently, small molecules have been shown to stimulate neurite outgrowth in vivo. In individuals suffering from a neurological disease, this stimulation of neurite outgrowth protects neurons from further degeneration, and accelerates the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.*, 56, pp. 169–78 (1996); and B. S. McEwen et al., *Brain Res. Dev. Brain. Res.*, 87, pp. 91–95 (1995)]. The progress of Alzheimer's disease is slowed in women who take estrogen. Estrogen is hypothesized to complement NGF and other neurotrophins and thereby help neurons differentiate and survive.

Tacrolimus, an immunosuppressive drug, has been demonstrated to act synergistically with NGF in stimulating neurite outgrowth in PC12 cells as well as sensory ganglia [Lyons et al., *PNAS*, 91, pp. 3191–3195 (1994)]. This compound has also been shown to be neuroprotective in focal cerebral ischemia [J. Sharkey and S. P. Butcher, *Nature*, 371, pp.336–339 (1994)] and to increase the rate of axonal regeneration in injured sciatic nerve [Gold et al., *J. Neurosci.*, 15, pp. 7509–16 (1995)].

Though a wide variety of neurological degenerative disorders may be treated by stimulating neurite outgrowth, there are relatively few agents known to possess these properties. Thus, there remains a great need for new pharmaceutically acceptable compounds and compositions that have the ability to stimulate neurite outgrowth in patients.

SUMMARY OF THE INVENTION

Applicants have solved the above problem by discovering that compounds invented by one of the co-applicants for use in reversing multi-drug resistance previously also surprisingly and unexpectedly possess neurotrophic activity. These amino acid derivatives are disclosed in U.S. Pat. No. 5,543,423.

These compounds stimulate neurite outgrowth in the presence of exogenous or endogenous NGF. The compositions disclosed herein comprise a compound from the genera described above and a neuronal growth factor. The methods to stimulate neurite outgrowth disclosed herein employ the above amino acid derivatives either alone or in combination with a neuronal growth factor. The methods are useful in treating nerve damage caused by various neurological diseases and physical traumas and also in ex vivo nerve regeneration.

DETAILED DESCRIPTION OF THE INVENTION

The present invention provides pharmaceutical compositions which comprise three components. The first component is a compound having the formula (I):

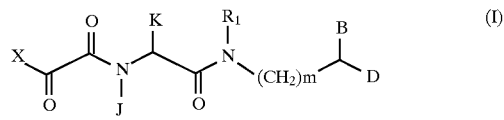

and pharmaceutically acceptable derivatives thereof, wherein $R_1$, B and D are independently selected from hydrogen, Ar, (C1–C6) straight or branched alkyl, (C2–C6) straight or branched alkenyl or alkynyl, (C5–C7) cycloalkyl-substituted (C1–C6) straight or branched alkyl, (C5–C7) cycloalkyl-substituted (C3–C6) straight or branched alkenyl or alkynyl, (C5–C7) cycloalkenyl-substituted (C1–C6) straight or branched alkyl, (C5–C7) cycloalkenyl-substituted (C3–C6) straight or branched alkenyl or alkynyl, Ar-substituted (C1–C6) straight or branched alkyl, or Ar-substituted (C3–C6) straight or branched alkenyl or alkynyl; provided that $R_1$ is not hydrogen.

Any one of the $CH_2$ groups in the alkyl chains is of $R_1$, B and D is optionally replaced by a heteroatom selected from O, S, SO, $SO_2$ and NR; wherein R is hydrogen, (C1–C6) straight or branched alkyl, (C3–C4) straight or branched alkenyl or alkynyl, or (C1–C4) bridging-alkyl. The (C1–C4) bridging alkyl, together with the nitrogen and a carbon atom of said heteroatom-containing chain, form a ring. That ring may also be optionally fused to an Ar group.

Preferably, B and D are independently selected from H, 3-Pyr—(CH$_2$)$_3$—, 4-Pyr—(CH$_2$)$_2$—, 3-Im—(CH$_2$)$_2$—, and Ph—(CH$_2$)$_2$—. R$_1$ is preferably selected from CH$_3$—, PhCH$_2$—, 4-Cl—PhCH$_2$—, 4-F—PhCH$_2$—, 4-PyCH$_2$—, and 1H—Im—CH$_2$—.

Each Ar is independently selected from phenyl, 1-naphthyl, 2-naphthyl, indenyl, azulenyl, fluorenyl and anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl or phenoxazinyl.

Preferred Ar groups of this invention are phenyl, 2-pyridyl, 3-pyridyl, 4-pyridyl, imidazolyl, indolyl, isoindolyl, quinolinyl, isoquinolinyl, 1,2,3,4-tetrahydroisoquinolinyl, and 1,2,3,4-tetrahydroquinolinyl.

Any Ar may be optionally substituted with one to three substituents independently selected from halogen, hydroxyl, nitro, —SO$_3$H, trifluoromethyl, trifluoromethoxy, (C1–C6) straight or branched alkyl, O—((C1–C6) straight or branched alkyl), O-benzyl, O-phenyl, 1,2-methylenedioxy, —NR5R6, carboxyl, N—((C1–C6) straight or branched alkyl, N—((C3–C5) straight or branched alkenyl) carboxamide, N,N-di-((C1–C6) straight or branched alkyl), N,N-di-((C3–C5) straight or branched alkenyl), carboxamide, morpholinyl, piperidinyl, O—H, CH$_2$—(CH$_2$)$_q$—M, O—(CH$_2$)$_q$—M, (CH$_2$)$_q$—O—M, or CH=CH—M. R$_5$ and R$_6$ are independently selected from hydrogen, (C1–C6) straight or branched alkyl, (C2–C6) straight or branched alkenyl or alkynyl or benzyl. Alternatively, R$_5$ and R$_6$ may be taken together to form a 5–7 membered heterocyclic ring. M is selected from 4-methoxyphenyl, 2-pyridyl, 3-pyridyl, 4-pyridyl, pyrazyl, quinolyl, 3,5-dimethylisoxazoyl, 2-methylthioazoyl, thiazoyl, 2-thienyl, 3-thienyl, 4-thienyl or pyrimidyl; and q is 0–2.

Preferred Ar substituents are halogen, hydroxyl, nitro, —SO$_3$H, trifluoromethyl, (C1–C6) straight or branched alkyl, O—((C1–C6) straight or branched alkyl) and —NR$_5$R$_6$.

Component J in formula (I) is selected from (C1–C6) straight or branched alkyl, (C3–C6) straight or branched alkenyl or alkynyl, Ar-substituted (C1–C6) straight or branched alkyl, Ar-substituted (C3–C6) straight or branched alkenyl or alkynyl, or cyclohexylmethyl. Preferably, J is methyl.

K is selected from (C1–C6) straight or branched alkyl, Ar substituted (C1–C6) straight or branched alkyl, (C2–C6) straight or branched alkenyl or alkynyl, or Ar-substituted (C3–C6) straight or branched alkenyl or alkynyl. Preferably, K is selected from phenylmethyl, 4-chloro-phenylmethyl and isopropyl.

Alternatively, J and K are taken together with the nitrogen and carbon atoms to which they are respectfully bound to form a 5–7 membered heterocyclic ring which may contain a heteroatom selected from O, S, SO and SO$_2$;

X is selected from Ar, —OR$_2$, or —NR$_3$R$_4$; wherein R$_2$ has the same definition as R$_1$; and R$_3$ and R$_4$ independently have the same definitions as B and D. Alternatively, R$_3$ and R$_4$ may be taken together to form a 5–7 membered heterocyclic aliphatic or aromatic ring. Preferably, X is 3,4,5-trimethoxyphenyl.

Component m is 0 or 1, preferably 0.

The compounds of this invention include all optical and racemic isomers.

A "pharmaceutically acceptable derivative," as used herein denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote or augment neurite outgrowth.

According to a preferred embodiment, the pharmaceutical compositions of the present invention comprise a compound having formula (II):

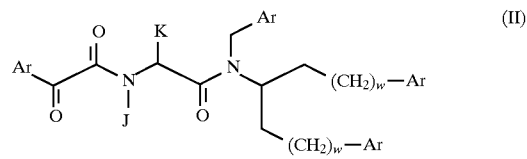

and pharmaceutically acceptable derivatives thereof, wherein J and K are independently selected from (C1–C6) straight or branched alkyl, or Ar-substituted (C1–C6) straight or branched alkyl; and w is 1 or 2.

Another preferred pharmaceutical composition of the present invention comprise a compound of formula (I), wherein at least one of B or D is represented by the formula —(CH$_2$)$_r$—Z—(CH$_2$)$_s$—Ar, wherein each Z is independently selected from O, S, SO, SO$_2$ or NR; and R is selected from hydrogen, (C1–C4) straight or branched alkyl, (C3–C4) straight or branched alkenyl or alkynyl, and (C1–C4) bridging alkyl wherein a bridge is formed between the nitrogen and the Ar group.

Another preferred embodiment of these compositions comprise a compound having formula (III):

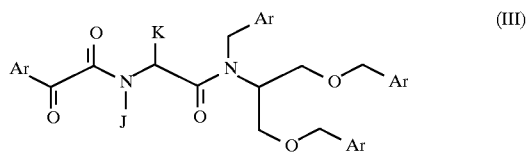

and pharmaceutically acceptable derivatives thereof, wherein J and K are independently selected from (C1–C6) straight or branched alkyl, or Ar-substituted (C1–C6) straight or branched alkyl; and w is 1 or 2. Table I provides examples of preferred compounds of the invention.

TABLE I (I')

[Structure: 3,4,5-trimethoxyphenyl-C(=O)-C(=O)-N(CH₃)-CH(K)-C(=O)-N(R₁)-CH(B)(D)]

| Cmpd | B | D | K | R₁ |
|------|---|---|---|-----|
| 6 | 4-Pyr—(CH₂)₂— | 4-Pyr—(CH₂)₂— | PhCH₂— | 4-F—PhCH₂— |
| 7 | 4-Pyr—(CH₂)₂— | 4-Pyr—(CH₂)₂— | PhCH₂— | PhCH₂— |
| 8 | 4-Pyr—(CH₂)₂— | 4-Pyr—(CH₂)₂— | PhCH₂— | 4-Cl—PhCH₂— |
| 9 | 4-Pyr—(CH₂)₂— | 4-Pyr—(CH₂)₂— | 4-Cl—PhCH₂— | PhCH₂— |
| 10 | H | Ph—(CH₂)₃— | PhCH₂— | 4-PyCH₂— |
| 12 | 3-Pyr—(CH₂)₃— | 3-Pyr—(CH₂)₃— | PhCH₂— | PhCH₂— |
| 14 | 4-Pyr—(CH₂)₂— | 4-Pyr—(CH₂)₂— | PhCH₂— | CH₃— |
| 15 | 3-Pyr—(CH₂)₃— | 3-Pyr—(CH₂)₃— | PhCH₂— | CH₃— |
| 16 | 4-Pyr—(CH₂)₂— | 4-Pyr—(CH₂)₂— | (CH₃)₂CH—CH₂— | PhCH₂— |
| 17 | 4-Pyr—(CH₂)₂— | 4-Pyr—(CH₂)₂— | (CH₃)₂CH—CH₂— | 4-F—PhCH₂— |
| 18 | 4-Pyr—(CH₂)₂— | 4-Pyr—(CH₂)₂— | (CH₃)₂CH—CH₂— | 4-Cl—PhCH₂— |
| 19 | 4-Pyr—(CH₂)₂— | 4-Pyr—(CH₂)₂— | 4-Cl—PhCH₂— | 4-F—PhCH₂— |
| 21 | H | 3-im-(CH₂)₂— | PhCH₂— | PhCH₂— |
| 23 | Ph—(CH₂)₂— | Ph—(CH₂)₂— | PhCH₂— | 1H-im-CH₂— |

If pharmaceutically acceptable salts of the compounds are used, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The second component in each of the pharmaceutical compositions described above is a neurotrophic factor. The term "neurotrophic factor", as used herein, refers to compounds which are capable of stimulating growth or proliferation of nervous tissue. As used in this application, the term "neurotrophic factor" excludes the compounds described herein.

Numerous neurotrophic factors have been identified in the art and any of those factors may be utilized in the compositions of this invention. These neurotrophic factors include, but are not limited to, nerve growth factor (NGF), insulin growth factor (IGF-1) and its active truncated derivatives such as gIGF-1, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). The most preferred neurotrophic factor in the compositions of this invention is NGF.

The third component of the pharmaceutically acceptable compositions of this invention is a pharmaceutically acceptable carrier. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both, the compound and the neurotrophic factor that may be combined with the carrier materials to produce a single dosage form will vary depending upon the host treated, the particular mode of administration. The two active ingredients of the pharmaceutical compositions of this invention act synergistically to stimulate neurite outgrowth. Therefore, the amount of neurotrophic factor in such compositions will be less than that required in a monotherapy utilizing only that factor. Preferably, the compositions should be formulated so that a dosage of between 0.01–100 mg/kg body weight/day of the compound can be administered and a dosage of between 0.01–100 $\mu$g/kg body weight/day of the neurotrophic can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and neurotrophic factor in the composition.

According to another embodiment, this invention provides methods for stimulating neurite outgrowth. In one aspect of this embodiment, the method is used to stimulate neurite outgrowth in a patient and is achieved by administering to the patient a pharmaceutically acceptable composition comprising any of the compounds described above and a pharmaceutically acceptable carrier. The amount of compound utilized in these methods is between about 0.01 and 100 mg/kg body weight/day.

In another aspect of this embodiment, the method is used to stimulate nerve growth ex vivo. For this aspect, the compounds described above can be applied directly to the nerve cells in culture. This aspect of the invention is useful for ex vivo nerve regeneration.

According to an alternate embodiment, the method of stimulating neurite outgrowth comprises the additional step of treating a patient or ex vivo nerve cells in culture with a neurotrophic factor, such as those contained in the pharmaceutical compositions of this invention described above. This embodiment includes administering the compound and the neurotrophic agent in a single dosage form or in separate, multiple dosage forms when they are to be administered to a patient. If separate dosage forms are utilized, they may be administered concurrently, consecutively or within less than about 5 hours of one another.

The methods and compositions of this invention may be used to treat nerve damage caused by a wide variety of diseases or physical traumas. These include, but are not limited to, Alzheimer's disease, Parkinson's disease, ALS, multiple sclerosis, stroke and ischemia associated with stroke, neural paropathy, other neural degenerative diseases, motor neuron diseases, sciatic crush, peripheral neuropathy, particularly neuropathy associated with diabetes, spinal cord injuries and facial nerve crush.

In order that the invention described herein may be more fully understood, the following examples are set forth. It should be understood that these examples are for illustrative purposes only and are not to be construed as limiting this invention in any manner.

EXAMPLES

General Methods

Proton nuclear magnetic resonance ($^1$H NMR) spectra were recorded at 500 MHZ on a Bruker AMX 500. Chemical shifts are reported in parts per million (δ) relative to Me$_4$Si (δ0.0). Analytical high performance liquid chromatography was performed on either a Waters 600E or a Hewlett Packard 1050 liquid chromatograph.

Example 1

1,5-Di(pyridin-4-yl)-pent-1,4-dien-3-one (Compound 1)

To a solution of 1,3-acetone dicarboxylic acid (21.0 g, 0.144 mmol) in absolute ethanol (200 mL) was added dropwise 4-pyridine carboxaldehyde (30.8 g, 0.288 mmol). Gas evolution occurred throughout the addition. After stirring at room temperature for 2 h, the reaction was treated with concentrated hydrochloric acid (100 mL) and heated to 80° C. at which time a yellow precipitate slowly formed. An additional 500 mL of ethanol was added to allow for stirring of the suspension. After 1 hr at 80° C., the precipitate was collected by filtration, washed with ethanol and dried under vacuum to provide the desired product as a yellow solid. The resulting dihydrochloride salt was recrystallized form methylene chloride to provide pure compound 1.

Example 2

1,5-Di(pyridin-4-yl)-pentan-3-one (Compound 2)

To a slurry of Compound 1 (21.3 g, 67.4 mmol) in 1,4-dioxane (40 mL) was added triethylamine (48.1 mL, 0.346 mol), formic acid (6.54 mL, 0.145 mol) and 10% palladium on carbon (0.7 g) and the resulting mixture heated to reflux. After stirring at reflux for 1 hr, the reaction was cooled to room temperature filtered and concentrated in vacuo. The resulting residue was chromatographed over silica gel (elution with 5% methanol/methylene chloride) to provide the desired material.

Example 3

(4-Fluorobenzyl)-(3-(pyridin-4-yl)-1-(2-(pyridin-4-yl)ethyl)propyl)amine (Compound 3)

To a flask equipped with a Dean-Stark trap, was added compound 2 (12.46 g, 51.91 mmol), 4-fluorobenzylamine (5.93 mL, 51.91 mmol) and benzene (50 mL) and the resulting mixture was heated to reflux. After the collection of 930 μL of water, the reaction mixture was cooled and concentrated. The residue was taken up into ethanol (50 mL) and added to a slurry of sodium borohydride (2.96 g, 77.8 mmol) in ethanol (50 mL) and the mixture heated to 80° C. and stirred for 1 h. The reaction mixture was cooled and concentrated. The residue was taken up into water, acidified to pH 3.0 with 6N hydrochloric acid. The aqueous phase was washed with ethyl acetate (2x). The aqueous phase was made basic with sodium hydroxide to a pH of 10 and the product extracted with methylene chloride (2x). The organics were combined, washed with brine, dried over anhydrous magnesium sulfate, filtered and concentrated in vacuo. Chromatography of the residue over silica gel (elution with 5% methanol/methylene chloride) provided compound 3.

Example 4

(S)-N-(4-Fluorobenzyl)-2-(N-methyl-N-tert-butylcarbamoyl)amino-3-phenyl-N-(3-(pyridin-4-yl)-1-(2-(pyridin-4-yl)-ethyl)propyl)propionamide (Compound 4)

To a solution of compound 3 (550 mg, 1.66 mmol) and (L)-BOC-N-methyl-phenylalanine (700 mg, 2.5 mmol) in methylene chloride (4.0 mL) containing diisopropylethylamine (300 μL, 1.72 mmol) was added (3-dimethylaminopropyl)-3-ethylcarbodiimide hydrochloride (480 mg, 2.5 mmol) and the reaction was allowed to stir for 48 h. The reaction was diluted with ethyl acetate and water. The layers were separated and the aqueous phase reextracted with ethyl acetate. The organics were combined, washed with saturated sodium bicarbonate, water and brine, dried over anhydrous magnesium sulfate, filtered and concentrated in vacuo. Chromatography of the residue over silica gel (elution with 5% methanol/methylene chloride) provided compound (4).

Example 5

(S)-N-(4-Fluorobenzyl)-2-methylamino-3-phenyl-N-(3-(pyridin-4-yl)-1-(2-(pyridin-4-yl)-ethyl)propyl) propionamide (Compound 5)

Compound 4 was dissolved in methylene chloride (10 mL) and treated with trifluoroacetic acid (4.0 mL). After stirring at room temperature for 1.5 h, the reaction was concentrated in vacuo. The residue was neutralized with saturated potassium carbonate and extracted with ethyl acetate (2x). The extracts were combined, washed with water, dried over anhydrous magnesium sulfate, filtered and concentrated in vacuo to provide Compound 5.

Example 6

(S)-N-(4-Fluorobenzyl)-2-(methyl-(2-oxo-2-(3,4,5-tri-methoxyphenyl)acetyl)amino)-3-phenyl-N-(3-(pyridin-4-yl)-1-(2-(pyridin-4-yl)-ethyl)propyl) propionamide (Compound 6)

To a solution of compound 5 (500 mg, 0.98 mmol) and 3,4,5-trimethoxybenzyolformic acid (294 mg, 1.22 mmol) in methylene chloride (4.0 mL) containing N,N-dimethylformamide (0.4 mL) was added (3-dimethylaminopropyl)-3-ethylcarbodiimide hydrochloride (235 mg, 1.22 mmol) and the reaction was allowed to stir for 24 h. The reaction was diluted with ethyl acetate and water. The layers were separated and the aqueous phase reextracted with ethyl acetate. The organics were combined, washed with saturated sodium bicarbonate, water and brine, dried over anhydrous magnesium sulfate, filtered and concentrated in vacuo. The residue was chromatographed on silica gel (elution with 5% methanol/methylene chloride) to provide the desired product. $^1$H NMR as a mixture of rotomers (500 MHz, CDCl$_3$) δ8.48–8.44 (m), 8.38 (dd), 7.36–7.33 (m), 7.28–7.18 (m), 7.13–7.02 (m), 6.97–6.87 (m), 6.58 (d), 6.00 (dt), 5.81 (t), 4.97 (br, s), 4.81 (d), 4.23–4.16 (m), 3.93 (s), 3.90 (s), 3.85 (s), 3.76 (s), 3.59 (dd), 3.28 (dd), 3.20 (s), 3.15 (s), 3.04–2.96 (m), 3.02 (s), 3.01 (s), 2.94 (dd), 2.63 (dt), 2.53–2.37 (m), 1.92–1.78 (m), 1.72–1.62 (m), 1.52–1.42 (m).

Example 7

(S)-N-Benzyl-2-(methyl-(2-oxo-2-(3,4,5-trimethoxyphenyl)acetyl)amino)-3-phenyl-N-(3-(pyridin-4-yl)-1-(2-pyridin-4-yl-ethyl)propyl) propionamide (Compound 7)

Compound 7 was prepared according to the protocols of Examples 3–6, by replacing 4-fluorobenzylamine with benzylamine. $^1$H NMR as a mixture of rotomers (500 MHz, CDCl$_3$) δ8.48 (dd), 8.53 (dd), 8.43 (dd), 8.35 (dd), 7.38 (d), 7.30–7.18 (m), 7.17–7.02 (m), 6.93 (s), 6.89 (d), 6.54 (d), 6.03 (dd), 5.86 (t), 5.08 (br,d), 4.88 (d), 4.32–4.18 (m), 3.95 (s), 3.89 (s), 3.86 (s), 3.73 (s), 3.63 (dd), 3.23–3.19 (m), 3.09 (dd), 3.05 (s), 3.03 (s), 2.97 (dd), 2.63 (dt), 2.57–2.37 (m), 2.24 (dt), 2.06 (m), 1.95–1.76 (m), 1.74–1.63 (m), 1.54–1.44 (m).

Example 8

(S)-N-(4-Chlorobenzyl)-2-(methyl-(2-oxo-2-(3,4,5-tri-methoxyphenyl)acetyl)amino)-3-phenyl-N-(3-(pyridin-4-yl)-1-(2-(pyridin-4-yl)-ethyl)propyl) propionamide (Compound 8)

Compound 8 was prepared according to the protocols of Examples 3–6, by replacing 4-fluorobenzylamine with 4-chlorobenzylamine. $^1$H NMR as a mixture of rotomers (500 MHz, CDCl$_3$) δ8.49 (dt), 8.45 (dd), 8.40 (dd), 7.69 (d), 7.31–7.14 (m), 7.12 (s), 7.08–7.03 (m), 6.98 (s), 6.94–6.91 (m), 6.85 (d), 6.02 (dd), 5.79 (t), 4.99 (br d), 4.83 (d), 4.22–4.16 (m), 3.96 (m), 3.91 (s), 3.88 (s), 3.87 (s), 3.81 (s), 3.78 (s), 3.61 (dd), 3.33 (dd), 3.21 (s), 3.17 (s), 3.04 (s), 3.03 (s), 3.03–3.00 (m), 2.95 (dd), 2.65 (dt), 2.56–2.40 (m), 2.28 (dt), 1.90–1.80 (m), 1.75–1.66 (m), 1.52–1.43 (m).

Example 9

(S)-N-Benzyl-3-(4-chlorophenyl)-2-(methyl-(2-oxo-2-(3,4,5-trimethoxyphenyl)acetyl)amino)-N-(3-(pyridin-4-yl)-1-(2-(pyridin-4-yl)-ethyl)propyl) propionamide (Compound 9)

Compound 9 was prepared according to the protocols of Examples 3–6, by replacing 4-fluorobenzylamine with benzylamine and (L)-BOC-N-methylphenylalanine with (L)-BOC-N-methyl-4-chlorophenylalanine. $^1$H NMR as a mixture of rotomers (500 MHz, CDCl$_3$) δ8.48 (dd), 8.45 (dt), 8.38 (dd), 7.32–6.87 (m), 6.58 (d), 5.94 (dd), 5.78 (t), 5.05 (brd), 4.83 (d), 4.26 (dd), 4.15 (m), 3.97 (s), 3.89 (s), 3.86 (s), 3.75 (s), 3.57 (dd), 3.20(s), 3.15 (s), 3.15–3.09 (m), 3.05–2.96 (m), 3.01 (s), 3.00 (s), 2.91 (dd), 2.65–2.38 (m), 2.26 (dt), 1.94–1.47 (m).

Example 10

(S)-2-(Methyl-(2-oxo-2-(3,4,5-trimethoxyphenyl)acetyl)amino)-3-phenyl-N-(4-phenylbutyl)-N-[(pyridin-4-yl)-methyl] propionamide (Compound 10)

Compound 10 was prepared according to the protocols of Examples 3–6, by replacing 4-fluorobenzylamine with 4-phenylbutylamine and compound 2 with 4-pyridinecarboxaldehyde. $^1$H NMR as a mixture of rotomers (500 MHz, CDCl$_3$) δ8.46 (dd), 8.42 (dd), 7.30–7.23 (m), 7.18–7.11 (m), 7.11 (s), 7.10 (s), 6.90 (d), 6.77 (d), 5.88 (t), 5.60 (dd), 4.85 (d), 4.50 (d), 4.28 (d), 3.93 (s), 3.83 (s), 3.81 (s), 3.80 (s), 3.65–3.50 (m), 3.37 (m), 3.20–3.15 (m), 3.08–3.06 (m), 3.06 (s), 3.05 (s), 2.92 (dd), 2.60 (m), 2.54 (m), 1.60–1.48 (m), 1.38–1.28 (m).

Example 11

1,7-Di(pyridin-4-yl)-heptan-4-one (Compound 11)

To a solution of 1,7-di(pyridin-4-yl)-heptan-4-ol (4.1 g, 15.2 mmol) in methylene chloride (50 mL) at 0° C., was added potassium bromide (180 mg) and 2,2,6,6-tetramethyl-1-piperidinyloxy, free radical (71 mg). To the resulting mixture was added dropwise a solution of sodium bicarbonate (510 mg) in sodium hypochlorite (65 ml). After the addition was complete, the reaction mixture was warmed to room temperature and stirred for 30 min. The mixture was diluted with ethyl acetate and water. The layers were separated and the aqueous layer reextracted with ethyl acetate. The organics were combined, washed with water and brine, dried over anhydrous magnesium sulfate, filtered and concentrated in vacuo. Chromatography of the residue over silica gel (elution with 5% methanol/methylene chloride) provided compound 11.

Example 12

(S)-N-Benzyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (Compound 12)

Compound 12 was prepared according to the protocols of Examples 3–6, by replacing 4-fluorobenzylamine with benzylamine and compound 2 with compound 11. $^1$H NMR as a mixture of rotomers (500 MHz, CDCl$_3$) δ8.43–8.38 (m), 8.30 (m), 8.16 (m), 7.53–7.45 (m) 7.34 (m), 7.32 (m), 7.26–7.22 (m), 7.19–7.07 (m), 7.00–6.83 (m), 5.89 (dd), 5.72 (t), 4.90 (d), 4.72 (d), 4.10 (d), 4.00 (d), 3.93 (s), 3.91 (s), 3.85 (s), 3.74 (s), 3.52 (dd), 3.16–3.10 (m), 3.04 (s), 2.99 (dd), 2.93 (s), 2.84 (dd), 2.67 –2.38 (m), 2.30 (m), 2.22 (m), 1.63–1.12 (m), 0.94 (m)

Example 13

Methyl-(3-(pyridin-4-yl)-1-(2-(pyridin-4-yl)-ethyl) propyl)amine (Compound 13)

To a slurry of methylamine hydrochloride (1.7 g, 25.4 mmol) and sodium acetate (2.5 g, 30.48 mmol) in methanol (20 mL) was added a solution of compound 2 (1.21 g, 5.08 mmol) in methanol (5 mL). The resulting mixture was treated with a solution of sodium cyanoborohydride (370 mg, 6.09 mmol) in methanol (5 mL) and heated to 80° C. After 1 h at 80° C., the reaction was cooled to room temperature and concentrated in vacuo. The residue was taken up into methylene chloride and 2N sodium hydroxide. The layers were separated and the organic phase washed with brine, dried over anhydrous magnesium sulfate, filtered and concentrated in vacuo to provide Compound 13.

Example 14

(S)-N-Methyl-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl) propionamide (Compound 14)

Compound 14 was prepared according to the protocols of Examples 4–6, by replacing compound 3 with compound 13. $^1$H NMR as a mixture of rotomers (500 MHz, CDCl$_3$) δ 8.50–8.46 (m), 8.37 (d), 7.32–7.26 (m), 7.21–7.16(m), 7.10–7.06 (m), 6.97 (dd), 6.93 (d), 5.93 (d), 5.54 (t), 4.72 (br,s), 4.17 (m), 3.94 (s), 3.92 (s), 3.84 (s), 3.82 (s), 3.51 (dd), 3.38 (dd), 3.29 (s), 3.11 (dd), 3.06 (s), 3.00 (s), 2.97

(dd), 2.86 (s), 2.82 (s), 2.49 (m), 2.37–2.23 (m), 2.17–1.98 (m), 1.85–1.55 (m)

Example 15

(S)-N-Methyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (Compound 15)

Compound 15 was prepared according to the protocols of Examples 13 and 14, by replacing compound 2 with compound 11. $^1$H NMR as a mixture of rotomers (500 MHz, CDCl$_3$) δ8.44–8.38 (m), 8.37–8.30 (m), 7.50–7.43 (m), 7.38–7.08 (m), 7.04 (s), 7.03–6.98 (m), 6.90–6.86 (m), 5.83 (dd), 5.74 (t) 4.75 (t), 4.65 (m), 3.94–3.93 (m), 3.92 (s), 3.90 (s), 3.84 (s), 3.83 (s), 3.44 (dd), 3.32 (dd), 3.20 (s), 3.01 (dd), 2.95 (s), 2.91 (s), 2.87 (dd), 2.59 (s), 2.58–2.37 (m), 1.68–1.00 (m).

Example 16

(S)-4-Methyl-2-(methyl-(2-oxo-2-(3,4,5-trimethoxyphenyl)acetyl)amino)pentanoic acid benzyl(3-(pyridin-4-yl)-1(2-(pyridin-4-yl) ethyl) propyl)amide (Compound 16)

Compound 16 was prepared according to the protocols of Examples 3–6, by replacing 4-fluorobenzylamine with benzylamine and (L)-BOC-N-methylphenylalanine with (S)-BOC-N-methylleucine.

Example 17

(S)-4-Methyl-2-(methyl-(2-oxo-2-(3,4,5-trimethoxyphenyl)acetyl)amino)pentanoic acid 4-fluorobenzyl(3-pyridin-4-yl-1-(2-pyridin-4-yl-ethyl) proply)amide (Compound 17)

Compound 17 was prepared according to the protocols of Examples 4–6, by replacing (L)-Boc-N-methylphenylalamine with (S)-Boc-N-methylleucine. $^1$H NMR as a mixture of rotomers (500 MHz, CDCl$_3$) δ8.48 (m), 8.45 (d), 7.32 (m), 7.18 (s), 7.12 (s), 7.09–6.92 (m), 6.84 (d), 5.72 (dd), 5.48 (dd), 4.99 (br d), 4.68 (d), 4.42 (d), 4.36 (d), 4.29 (m), 3.94 (s), 3.91 (s), 3.87 (s), 3.83 (s), 2.96 (s), 2.92 (s), 2.69 (dt), 2.62–2.55 (m), 2.52–2.44 (m), 2.12–1.73 (m), 1.63–1.57 (m), 1.48–1.39 (m), 1.23 (m), 1.03 (t), 0.90 (d), 0.69 (d)

Example 18

(S)-4-Methyl-2-(methyl-(2-oxo-2-(3,4,5-trimethoxyphenyl)acetyl)amino)pentanoic acid 4-chlorobenzyl(3-pyridin-4-yl-1-(2-pyridin-4-yl-ethyl) propyl)amide (Compound 18)

Compound 18 was prepared according to the protocols of Examples 3–6, by replacing 4-fluorobenzylamine with 4-chlorobenzylamine and (L)-Boc-N-methylphenylalanine with (S)-Boc-N-methylleucine. $^1$H NMR as a mixture of rotomers (500 MHz, CDCl$_3$) δ8.50 (m), 8.47 (d), 7.38 (d), 7.30–7.26 (m), 7.19 (s), 7.13 (s), 7.10 (d), 7.04 (d), 6.98 (d), 6.84 (d), 5.73 (dd), 5.47 (dd), 5.03 (br d), 4.69 (d), 4.42 (d), 4.36 (d), 4.31 (m), 3.95 (s), 3.93 (s), 3.88 (s), 3.84 (s), 2.97 (s), 2.94 (s), 2.70 (dt), 2.63–2.43 (m), 2.12–1.56 (m), 1.48–1.40 (m), 1.25 (m), 1.04 (t), 0.91 (d), 0.70 (d).

Example 19

(S)-N-(4-fluorobenzyl)-3-(4-chlorophenyl)-2-(methyl-(2-oxo-2-(3,4,5-trimethoxyphenyl)acetyl) amino)-N-(3-pyridin-4-yl-1-(2-pyridin-4-yl-ethyl) propyl)propion-amide (Compound 19)

Compound 19 was prepared according to the protocols of Examples 4–6, by replacing (L)-Boc-N-methylphenylalanine with (L)-Boc-N-methyl-4-chlorophenylalanine. $^1$H NMR as a mixture of rotomers (500 MHz, CDCl$_3$) δ8.49–8.41 (m), 7.34 (s), 7.28–7.20 (m), 7.10–6.90 (m), 6.64 (d), 5.92 (dd), 5.74 (t), 4.95 (br d), 4.74 (d), 4.24–4.13 (m), 3.94 (s), 3.90 (s), 3.86 (s), 3.77 (s), 3.54 (dd), 3.23–3.17 (m), 2.99 (s), 2.98 (s), 2.90 (d), 2.63 (dt), 2.59–2.37 (m), 2.28 (dt), 1.94–1.70 (m), 1.57–1.47 (m).

Example 20

(4-Chlorobenzyl)-(3-imidazol-1-yl-propyl)amine (Compound 20)

To a solution of 1-(3-amino-propyl)imidazole (2.1 g, 16.8 mmol), diisopropyl-ethylamine (3.5 mL, 20.0 mmol) and 4-N,N-dimethyl-aminopyridine (200 mg, 1.7 mmol) in methylene chloride (15 mL) at 0° C. was added dropwise 4-chlorobenzoyl-chloride (2.1 mL, 16.8 mmol). The reaction was then allowed to warm to room temperature. After 5 hours, the reaction was diluted with methylene chloride, washed with 1N sodium hydroxide, brine, dried over anhydrous magnesium sulfate, filtered and concentrated in vacuo to provide a white solid. This material was washed with diethyl ether to provide N-(3-imidazol-1-yl-propyl)-4-chlorobenzamide. To a slurry of the above amide (1.58 g, 6.0 mmol) in tetrahydrofuran (30 mL) was slowly added lithium aluminum hydride (456 mg, 12.0 mmol) upon which the reaction became exothermic. The mixture was heated to 80° C., stirred for 1 hr, cooled to 0° C. and quenched by addition of water (0.5 mL), 15% sodium hydroxide (0.5 mL) and an additional 1.5 mL of water. The reaction was diluted with ethyl acetate, dried over anhydrous magnesium sulfate, filtered and concentrated in vacuo to provide compound 20.

Example 21

(S)-N-(4-chlorobenzyl)-N-(3-imidazol-1-yl-propyl)-2-(methyl-(2-oxo-2-(3,4,5-trimethoxyphenyl)acetyl) amino)-3-phenylpropionamide (Compound 21)

Compound 21 was prepared according to the protocols of Examples 4–6, by replacing compound 3 with compound 20. $^1$H NMR as a mixture of rotomers (500 MHz, CDCl$_3$) δ8.48 (m), 7.44 (br s), 7.37 (br s), 7.30–7.16 (m), 7.10–7.02 (m), 6.95 (d), 6.83 (m), 5.78 (t), 5.72 (t), 4.77 (d), 4.57 (d), 4.26 (dd), 3.94 (s), 3.93 (s), 3.88–3.77 (m), 3.80 (s), 3.48 (dt), 3.42–3.33 (m), 3.19–3.14 (m), 3.13 (s), 3.12 (s), 3.13–2.97 (m), 2.89 (t), 2.80 (m), 2.74 (t), 2.65 (m), 2.08–1.98 (m), 1.90 (m), 1.80–1.60 (m).

Example 22

N-(1H-Imidazol-2-yl-methyl)-N-(1-phenethyl-3-phenylpropyl)amine (Compound 22)

To a solution of 1,5-Diphenylpentan-3-one (5.26 g, 22.1 mmol), ammonium acetate (8.52 g, 110.5 mmol) and sodium acetate (9.06 g, 110.5 mmol) in methanol (80 mL) was added a solution of sodium cyanoborohydride (1.67 g, 26.52 mmol) in methanol (20 mL) and the reaction heated to reflux. After stirring at reflux for 30 min, the reaction was cooled and concentrated to dryness. The residue was partioned between methylene chloride and 2N sodium hydroxide. The organic phase was separated, washed with brine, dried over anhydrous magnesium sulfate, filtered and concentrated in vacuo. Chromatography of the residue on silica gel (elution with 2–5% methanol/methylene chloride) provided N-(1-phenethyl-3-phenyl-propyl)amine. To a solution of the above amine (2.1 g, 8.82 mmol) in ethanol (50 mL), was added 2-imidazole-carboxaldehyde (813 mg, 8.47 mmol) and the reaction heated to 50° C. After stirring for 2 hr, the resulting homogeneous solution was treated with sodium borohydride (400 mg, 10.58 mmol) and allowed to stir overnight. The reaction was concentrated to dryness and the residue was partioned between methylene chloride and 2N sodium hydroxide. The organic phase was separated, washed with brine, dried over anhydrous magnesium sulfate, filtered and concentrated in vacuo. Chromatography of the residue on silica gel (elution with 5% methanol/methylene chloride) provided compound 22.

Example 23

(S)-N-(1H-Imidazol-2-yl-methyl)-2-(methyl-(2-oxo-2-(3,4,5-trimethoxyphenyl)acetyl)amino)-N-(1-phenethyl-3-phenyl-propyl)3-phenyl-propionamide (Compound 23)

Compound 23 was prepared according to the protocols of Examples 4–6, by replacing compound 3 with compound 22. $^1$H NMR as a mixture of rotomers (500 MHz, CDCl$_3$) δ7.40–7.00 (m), 6.95–6.87 (m), 5.95 (t), 5.69 (t), 4.66 (d), 4.46 (d), 4.12 (m), 3.94 (s), 3.92 (s), 3.82 (s), 3.81 (s), 3.80 (s), 3.47 (s), 3.43 (dd), 3.34 (dd), 3.22 (s), 3.15 (s), 3.03 (dd), 3.00 (s), 2.60 (dt), 2.45–2.22 (m), 1.80–1.78 (m).

Example 24

In order to directly determine the neurotrophic activity of compounds described in this invention, the neurite outgrowth assay was carried out with pheochromocytoma PC12 cells as described by Lyons et al.(1994).

PC12 cells are maintained at 37 degree and 5% CO2 in Dulbecco's modified Eagle's medium (DMEM) supplemented with 10% heat-inactivated horse serum, 5% heat-inactivated fetal bovine serum (FBS), and 1% glutamate. The cells are then plated at $10^5$ per well in 96 well plates coated with 5 μg/cm$^2$ rat tail collagen and allowed to attach overnight. The medium is then replaced with DMEM, 2% heat-inactivated horse serum, 1% glutamate, 1–5 ng/ml of NGF (Sigma) and varying concentrations of compound (0.1 nM–10 nM). The background control culture is administered with 105 ng/ml of NGF alone without compound. Positive control cultures are administered with high concentration of NGF (50 ng/ml).

The compounds described in this invention herein cause a significant increase in neurite outgrowth over background control cultures.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:
1. A pharmaceutically acceptable composition comprising:
a) a neurotrophic amount of a compound having the formula (I):

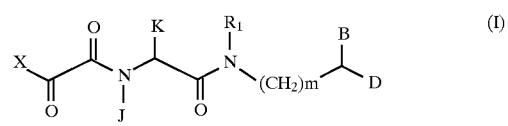

and pharmaceutically acceptable derivatives thereof, wherein:

$R_1$, B and D are independently: hydrogen, Ar, (C1–C6) straight or branched alkyl, (C2–C6) straight or branched alkenyl or alkynyl, (C5–C7) cycloalkyl substituted (C1–C6) straight or branched alkyl, (C5–C7) cycloalkyl substituted (C3–C6) straight or branched alkenyl or alkynyl, (C5–C7) cycloalkenyl substituted (C1–C6) straight or branched alkyl, (C5–C7) cycloalkenyl substituted (C3–C6) straight or branched alkenyl of alkynyl, Ar-substituted (C1–C6) straight or branched alkyl, Ar-substituted (C3–C6) straight or branched alkenyl or alkynyl;

provided that $R_1$ is not hydrogen;

wherein any one of the $CH_2$ groups of said alkyl chains in $R_1$, B and D is optionally replaced by O, S, SO, $SO_2$ or NR;

wherein R is hydrogen, (C1–C6) straight or branched alkyl, (C3–C4) straight or branched alkenyl or alkynyl, or (C1–C4) bridging-alkyl wherein a bridge is formed between the nitrogen and a carbon atom of said alkyl chain to form a ring, and wherein said ring is optionally fused to Ar;

wherein each Ar is independently selected from phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isotriazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroisoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl and phenoxazinyl; and wherein each Ar is optionally and independently substituted with one to three substituents independently selected from hydrogen, halogen, hydroxyl, nitro, —$SO_3H$, trifluoromethyl, trifluoromethoxy, (C1–C6) straight or branched alkyl, O—((C1–C6) straight or branched alkyl), O-benzyl, O-phenyl, 1,2-methylenedioxy, —$NR_5R_6$, carboxyl, N—(C1–C6 straight or branched alkyl or C3–C5 straight or branched alkenyl) carboxamides, N,N-di-((C1–C6) straight or branched alkyl or (C3–C5) straight or branched alkenyl), carboxamides, morpholinyl, piperidinyl, O—M, $CH_2$—$(CH_2)_q$—M, O—$(CH_2)_q$—M, $(CH_2)_q$—O—M, and CH=CH—M;

wherein $R_5$ and $R_6$ are independently selected from the group consisting of hydrogen, (C1–C6) straight or branched alkyl, (C2–C6) straight or branched alkenyl or alkynyl, and benzyl or $R_5$ and $R_6$ are taken together to form a 5–7 membered heterocyclic ring;

M is selected from the group consisting of 4-methoxyphenyl, 2-pyridyl, 3-pyridyl, 4-pyridyl, pyrazyl, quinolyl, 3,5-dimethylisoxazoyl, 2-methylthioazoyl, thiazoyl, 2-thienyl, 3-thienyl, 4-thienyl and pyrimidyl; and q is 0–2;

J is selected from the group consisting of (C1–C6) straight or branched alkyl, (C3–C6) straight or branched alkenyl or alkynyl, Ar-substituted (C1–C6) straight or branched alkyl, and Ar-substituted (C3–C6) straight or branched alkenyl of alkynyl, and cyclohexylmethyl;

K is selected from the group consisting of (C1–C6) straight or branched alkyl, Ar-substituted (C1–C6) straight or branched alkyl, (C2–C6) straight or branched alkenyl or alkynyl, and Ar-substituted (C3–C6) straight or branched alkenyl or alkynyl;

X is selected from the group consisting of Ar, —OR$_2$, and —N(R$_3$)R$_4$;

wherein R$_2$ has the same definition as R$_1$;

R$_3$ and R$_4$ independently have the same definitions as B and D; or R$_3$ and R$_4$ are taken together to form a 5–7 membered heterocyclic aliphatic or aromatic ring; and m is 0 or 1;

b) a neurotrophic factor; and c) a pharmaceutically suitable carrier.

2. The pharmaceutically acceptable composition according to claim 1, wherein said compound has the formula:

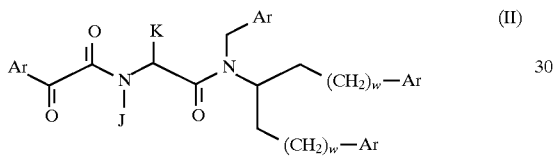

wherein:

J and K are independently (C1–C6) straight or branched alkyl, or Ar-substituted (C1–C6) straight or branched alkyl; and w is 1 or 2.

3. The pharmaceutically acceptable composition according to claim 1, wherein at least one of B or D is independently represented by the formula —(CH$_2$)$_r$—(Z)—(CH$_2$)$_s$—Ar, wherein:

r is 1–4;

s is 0–1; and each Z is independently selected from the group consisting of O, S, SO, SO$_2$ and NR; wherein R is selected from the group consisting of hydrogen, (C1–C4) straight or branched alkyl, (C3–C4) straight or branched alkenyl or alkynyl, and (C1–C4) bridging alkyl wherein a bridge if formed between the nitrogen and the Ar group.

4. The pharmaceutically acceptable composition according to claim 3, wherein said compound has the formula:

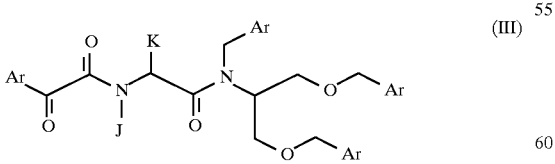

wherein:

J and K are independently (C1–C6) straight or branched alkyl, or Ar-substituted (C1–C6) straight or branched alkyl; and w is 1 or 2.

5. The pharmaceutically acceptable composition according to claim 1, wherein:

each Ar is independently selected from phenyl, 2-pyridyl, 3-pyridyl, 4-pyridyl, imidazolyl, indolyl, isoindoyl, quinolinyl, isoquinolinyl, 1,2,3,4-tetrahydroisoquinolinyl, and 1,2,3,4-tetrahydroquinolinyl; and each Ar optionally and independently contains one to three substituents independently selected from hydroxyl, nitro, trifluoromethyl, (C1–C6) straight or branched alkyl, O—((C1–C6) straight or branched alkyl), halogen, SO$_3$H, and —NR$_3$R$_4$.

6. The pharmaceutical composition according to claim 2, wherein said compound is selected from:

(S)-N-(4-Fluorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)-propionamide (Compound 6);

(S)-N-Benzyl-2-(methyl-(2-oxo-2-(3,4,5-trimethoxyphenyl)acetyl)amino)-3-phenyl-N-(3-(pyridin-4-yl)-1-(2-pyridin-4-yl-ethyl)propyl) propionamide (Compound 7);

(S)-N-(4-Chlorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)-propionamide (Compound 8);

(S)-N-Benzyl-3-(4-chlorophenyl)-2-(methyl-(2-oxo-2-(3,4,5-trimethoxyphenyl)acetyl)amino)-N-(3-(pyridin-4-yl)-1-(2-(pyridin-4-yl)-ethyl)propyl)propionamide (Compound 9);

(S)-2-(Methyl-(2-oxo-2-(3,4,5-trimethoxy-phenyl)acetyl)-amino)-3-phenyl-N-(4-phenylbutyl)-N-[(pyridin-4-yl)-methyl] propionamide (Compound 10);

(S)-N-Benzyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (Compound 12);

(S)-N-Methyl-2-(methyl-(2-oxo-2-(3,4,5-trimethoxyphenyl)acetyl)amino)-3-phenyl-N-(3-(pyridin- 4-yl)-1-(2-(pyridin-4-yl)-ethyl)propyl) propionamide (Compound 14);

(S)-N-Methyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (Compound 15);

(S)-4-Methyl-2-(methyl-(2-oxo-2-(3,4,5-trimethoxyphenyl)acetyl)amino)pentanoic acid-benzyl (3-(pyridin-4-yl)-1-(2-(pyridin-4-yl)ethyl)propyl) amide (Compound 16);

(S)-4-Methyl-2-(methyl-(2-oxo-2-(3,4,5-trimethoxyphenyl)acetyl)amino)pentanoic acid-4-fluorobenzyl (3-pyridin-4-yl-1-(2-pyridin-4-yl-ethyl) proply)amide (Compound 17);

(S)-4-Methyl-2-(methyl-(2-oxo-2-(3,4,5-trimethoxyphenyl)acetyl)amino)pentanoic acid-4-chlorobenzyl(3-pyridin-4-yl-1-(2-pyridin-4-yl-ethyl) propyl)amide (Compound 18);

(S)-N-(4-fluorobenzyl)-3-(4-chlorophenyl)-2-(methyl-(2-oxo-2-(3,4,5-trimethoxyphenyl)acetyl)amino)-N-(3-pyridin-4-yl-1-(2-pyridin-4-yl-ethyl)propyl)propionamide (Compound 19); or (S)-N-(4-chlorobenzyl)-N-(3-imidazol-1-yl-propyl)-2-(methyl-(2-oxo-2-(3,4,5-trimethoxyphenyl)acetyl) amino)-3-phenylpropionamide (Compound 21).

7. The pharmaceutical composition according to claim 6, wherein said compound is (S)-N-Benzyl-3-(4-chlorophenyl)-2-(methyl-(2-oxo-2-(3,4,5-trimethoxy-phenyl)acetyl)

amino)-N-(3-(pyridin-4-yl)-1-(2-(pyridin-4-yl)-ethyl) propyl)propionamide (compound 9).

8. The pharmaceutically acceptable composition according to claim 1, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotrophic factors (CNTF), glial cell-derived neurotrophic factor (GDNF), neurotrophin-3 (NT-3) and neurotrophin 4/5 (NT-4/5).

9. The pharmaceutically acceptable composition according to claim 8, wherein said neurotrophic factor is nerve growth factor (NGF).

10. A method for stimulating neurite growth in a patient or in an ex vivo nerve cell comprising the step of administering to said patient or said nerve a neurotrophic amount of a compound having the formula (I):

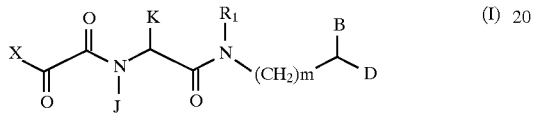

and pharmaceutically acceptable derivatives thereof, wherein:
$R_1$, B, D, J, K, X and m are defined as in claim 1.

11. The method according to claim 10, wherein said compound has the formula:

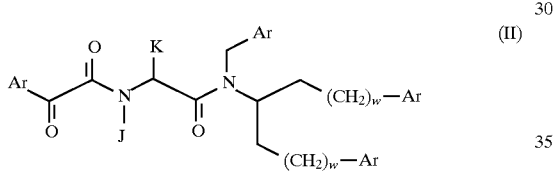

wherein:
J and K are independently selected from (C1–C6) straight or branched alkyl, or Ar-substituted (C1–C6) straight or branched alkyl; and
w is 1 or 2.

12. The method according to claim 10, wherein at least one of B or D is independently represented by the formula —(CH$_2$)$_r$—(Z)—(CH$_2$)$_s$—Ar, wherein:
r is 1–4;
s is 0–1; and
each Z is independently selected from the group consisting of O, S, SO, SO$_2$ and NR; wherein R is selected from the group consisting of hydrogen, (C1–C4) straight or branched alkyl, (C3–C4) straight or branched alkenyl or alkynyl, and (C1–C4) bridging alkyl wherein a bridge is formed between the nitrogen and the Ar group.

13. The method according to claim 12, wherein said compound has the formula:

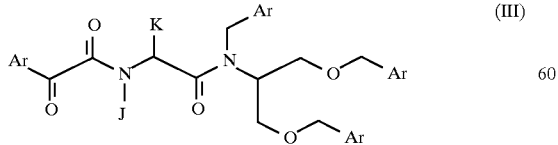

wherein:
J and K are independently selected from (C1–C6) straight or branched alkyl, or Ar-substituted (C1–C6) straight or branched alkyl; and w is 1 or 2.

14. The method according to claim 10, wherein:
each Ar is independently selected from phenyl, 2-pyridyl, 3-pyridyl, 4-pyridyl, imidazolyl, indolyl, isoindoyl, quinolinyl, isoquinolinyl, 1,2,3,4-tetrahydroisoquinolinyl, and 1,2,3,4-tetrahydroquinolinyl; and
each Ar optionally and independently contains one to three substituents independently selected from hydroxyl, nitro, trifluoromethyl, (C1–C6) straight or branched alkyl, O—((C1–C6) straight or branched alkyl), halogen, SO$_3$H, and —NR$_3$R$_4$.

15. The method according to claim 11, wherein said compound is selected from:
(S)-N-(4-Fluorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)-propionamide (compound 6);
(S)-N-Benzyl-2-(methyl-(2-oxo-2-(3,4,5-trimethoxyphenyl)acetyl)amino)-3-phenyl-N-(3-(pyridin-4-yl)-1-(2-pyridin-4-yl-ethyl)propyl) propionamide (compound 7);
(S)-N-(4-Chlorobenzyl)-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl)-propionamide (compound 8);
(S)-N-Benzyl-3-(4-chlorophenyl)-2-(methyl-(2-oxo-2-(3,4,5-trimethoxyphenyl)acetyl)amino)-N-(3-(pyridin-4-yl)-1-(2-(pyridin-4-yl)-ethyl)propyl)propionamide (compound 9);
(S)-2-(Methyl-(2-oxo-2-(3,4,5-trimethoxy-phenyl)acetyl)-amino)-3-phenyl-N-(4-phenylbutyl)-N-[(pyridin-4-yl)-methyl] propionamide (compound 10);
(S)-N-Benzyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (compound 12);
(S)-N-Methyl-2-(methyl-(2-oxo-2-(3,4,5-trimethoxyphenyl)acetyl)amino)-3-phenyl-N-(3-(pyridin-4-yl)-1-(2-(pyridin-4-yl)-ethyl)propyl) propionamide (compound 14);
(S)-N-Methyl-2-(methyl-(2-oxo-2-(3,4,5-trimethoxyphenyl)acetyl)amino)-3-phenyl-N-(3-(pyridin-4-yl)-1-(2-(pyridin-4-yl)-propyl)butyl) propionamide (compound 15);
(S)-4-Methyl-2-(methyl-(2-oxo-2-(3,4,5-trimethoxyphenyl)acetyl)amino)pentanoic acid-benzyl (3-(pyridin-4-yl)-1-(2-(pyridin-4-yl)ethyl) propyl) amide (compound 16);
(S)-4-Methyl-2-(methyl-(2-oxo-2-(3,4,5-trimethoxyphenyl)acetyl)amino)pentanoic acid-4-fluorobenzyl(3-pyridin-4-yl-1-(2-pyridin-4-yl-ethyl) proply)amide (compound 17);
(S)-4-Methyl-2-(methyl-(2-oxo-2-(3,4,5-trimethoxyphenyl)acetyl)amino)pentanoic acid-4-chlorobenzyl(3-pyridin-4-yl-1-(2-pyridin-4-yl-ethyl) propyl)amide (compound 18);
(S)-N-(4-fluorobenzyl)-3-(4-chlorophenyl)-2-(methyl-(2-oxo-2-(3,4,5-trimethoxyphenyl)acetyl)amino)-N-(3-pyridin-4-yl-1-(2-pyridin-4-yl-ethyl)propyl)propionamide (compound 19); or
(S)-N-(4-chlorobenzyl)-N-(3-imidazol-1-yl-propyl)-2-(methyl-(2-oxo-2-(3,4,5-trimethoxyphenyl)acetyl) amino)-3-phenylpropionamide (compound 21).

16. The method according to claim 15, wherein said compound is (S)-N-Benzyl-3-(4-chlorophenyl)-2-(methyl- (2-oxo-2-(3,4,5-trimethoxy-phenyl)acetyl)amino)-N-(3-(pyridin-4-yl)-1(2-(pyridin-4-yl)-ethyl)propyl)-propionamide (compound 9).

17. The method according to any one of claims 10–16, wherein said compound is administered to a patient and is formulated together with a pharmaceutically suitable carrier into a pharmaceutically acceptable composition.

18. The method according to claim 17, wherein said method is used to treat a patient suffering from Alzheimer's disease, Parkinson's disease, ALS, multiple sclerosis, stroke and ischemia associated with stroke, neural paropathy, other neural degenerative diseases, motor neuron diseases, sciatic crush, peripheral neuropathy, diabetic neuropathy, spinal cord injury or facial nerve crush.

19. The method according to claim 18, comprising the additional step of administering to said patient a neurotrophic factor either as part of a multiple dosage form with said compound or as a separate dosage form.

20. The method according to claim 19, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotrophic factors CNTF), glial cell-derived neurotrophic factor (GDNF), neurotrophin-3 (NT-3) and neurotrophin 4/5 (NT-4/5).

21. The method according to claim 20, wherein said neurotrophic factor is nerve growth factor (NGF).

22. The method according to any one of claim 18, wherein said patient is suffering from diabetes associated peripheral neuropathy.

23. The method according to any one of claims 10–16, wherein said method is used to stimulate ex vivo nerve regeneration.

24. The method according to claim 23, comprising the additional step of contacting said nerve cell with a neurotrophic factor.

25. The method according to claim 24, wherein said neurotrophic factor is selected from nerve growth factor (NGF), insulin growth factor (IGF) and active truncated derivatives thereof, acidic fibroblast growth factor (aFGF), basic fibroblast growth factor (bFGF), platelet-derived growth factors (PDGF), brain-derived neurotrophic factor (BDNF), ciliary neurotrophic factors (CNTF), glial cell-derived neurotrophic factor (GDNF), neurotrophin-3 (NT-3) and neurotrophin 4/5 (NT-4/5).

26. The method according to claim 25, wherein said neurotrophic factor is nerve growth factor (NGF).

* * * * *

UNITED STATES PATENT AND TRADEMARK OFFICE
CERTIFICATE OF CORRECTION

PATENT NO.   : 5,840,736
DATED        : November 24, 1998
INVENTOR(S)  : Zelle et al.

It is certified that error appears in the above-identified patent and that said Letters Patent is hereby corrected as shown below:

Title Page,
Item [56], Other Publications, in W.E. Lyons delete "Immunosupressant" and substitute therefor -- Immunosuppressant -- .

Column 3,
Line 38, delete "NR5R6" and substitute therefor -- $NR_5R_6$ -- .
Line 43, delete "O-H" and substitute therefor -- O-M --.
Line 59, and line 65 delete "from(C1-C6) " and substitute therefor -- from (C1-C6) -- .

Column 4,
Lines 44 and 54, delete "comprise" and substitute therefor -- comprises -- .

Column 5,
Table 1, compound 21, delete "3-im- $(CH_2)_2$" and substitute therefor -- 3-Im- $(CH_2)_2$ -- .
Table 1, compound 23, delete "1H-im-$CH_2$" and substitute therefor -- 1H-Im-$CH_2$ -- .

Column 6,
Line 37 delete "(NT-3)and " and substitute therefor -- (NT-3) and -- .

Column 9,
Line 33 delete "form" and substitute therefor -- from -- .

Column 12,
Line 63 delete "8" and insert -- $\delta$ -- .

UNITED STATES PATENT AND TRADEMARK OFFICE
CERTIFICATE OF CORRECTION

PATENT NO. : 5,840,736
DATED : November 24, 1998
INVENTOR(S) : Zelle et al.

It is certified that error appears in the above-identified patent and that said Letters Patent is hereby corrected as shown below:

Column 13,
Line 32, delete "proply) amide" and substitute therefor -- propyl) amide -- .

Column 18
Line 4, delete "and" and substitute therefor -- or -- .
Line 52, delete "proply) amide" and substitute therefor -- propyl) amide -- .

Column 20,
Line 12, delete "and" and substitute therefor -- or -- .
Line 53, delete "proply) amide" and substitute therefor -- propyl) amide -- .

Column 21,
Line 25, delete "CNTF)" and substitute therefor -- (CNTF) -- .

Column 22,
Line 5, delete "any one of ".

Signed and Sealed this

Twenty-first Day of August, 2001

Attest:

NICHOLAS P. GODICI
*Attesting Officer*  *Acting Director of the United States Patent and Trademark Office*